United States Patent [19]

Battais et al.

[11] Patent Number: 4,499,022
[45] Date of Patent: Feb. 12, 1985

[54] ORGANOMETALLIC TELOMERS, METHODS OF PREPARATION AND BIOCIDAL COMPOSITIONS OBTAINED

[75] Inventors: Alain Battais; Bernard J. L. Boutevin; Yves J. D. Pietrasanta, all of Montpellier, France

[73] Assignee: Etat Francais, Paris Armees, France

[21] Appl. No.: 393,413

[22] Filed: Jun. 29, 1982

[30] Foreign Application Priority Data

Jul. 3, 1981 [FR] France ............................... 81 13080

[51] Int. Cl.³ ................................................ C07F 7/22
[52] U.S. Cl. ............................. 260/429.7; 106/287.19; 106/15.05
[58] Field of Search ......................................... 260/429.7

[56] References Cited

U.S. PATENT DOCUMENTS

| | | | |
|---|---|---|---|
| 3,167,532 | 1/1965 | Leebrick | 260/429.7 |
| 3,555,148 | 1/1971 | Katsumura et al. | 260/429.7 X |
| 3,806,530 | 4/1974 | Dorfett et al. | 260/429.7 |
| 3,933,740 | 1/1976 | Hopkins et al. | 260/429.7 X |
| 4,058,544 | 11/1977 | Kushlefsky | 260/429.7 |
| 4,191,579 | 3/1980 | Hails et al. | 260/429.7 X |

Primary Examiner—Helen M. S. Sneed
Attorney, Agent, or Firm—Parkhurst & Oliff

[57] ABSTRACT

The invention concerns an organometallic telomer which can be used in particular as biocidal agent.

It is represented by the formula:

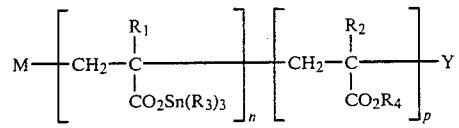

in which:
n and p represent numbers between 1 and 100 such that the ratio $n/(n+p)$ is less than or equal to 0.75;
$R_1$ and $R_2$ which are identical or different represent a hydrogen atom or a methyl group;
$R_3$ represents a linear or branched alkyl group having 1 to 12 carbon atoms, or a substituted or unsubstituted phenyl group;
$R_4$ represents a hydrogen atom or has one of the meanings indicated for $R_3$;
M and Y coming from a transfer agent in which Y represents hydrogen, chlorine or bromine and M an electro-attractive organic use.

Used for the control of parasitic and in particular marine organisms.

4 Claims, No Drawings

ORGANOMETALLIC TELOMERS, METHODS OF PREPARATION AND BIOCIDAL COMPOSITIONS OBTAINED

The field of art of the present invention is that of biocidal compositions containing organostannic groups intended to control the growth of parasitic organisms.

It is already known to use organostannic derivatives to control parasitic organisms, for instance bacteria, fungi, molds and more particularly marine organisms. It is also known that these derivatives have a certain toxicity which may be injurious to the surrounding environment. Thus, when using a paint which contains an organostannic derivative in order to control the growth of marine organisms the concentration of organostannic derivative rather rapidly becomes very high around the support covered by this paint due to the speed of lixiviation of the toxic element. One has therefore sought biocidal resins in which the active principle is combined with a polymer by covalent bond in order to decrease the speed of lixiviation and thereby increase the life of this type of paint for an amount of active principle comparable to that present in the paints now used.

French Pat. No. 1 384 699 and Canadian Pat. No. 989 998 describe bicidal compositions in which tin-containing molecules are fixed on support polymers or copolymers having reactive functions. The French patent describes a method of preparing biocidal resins in which different organometallic monomers are polymerized or copolymerized. The Canadian patent describes a method of synthesizing organostannic copolymers in which a support of high molecular weight which contains reactive functions is esterified with trialkyl or triaryl tin oxides or hydroxides.

The drawback of this type of composition resides in the fact that as a result of the hydrolysis of the tin-containing molecules and the formation of acids which results therefrom, a paint which contains this type of resin rapidly deteriorates as a result of the formation of plaques which detach themselves from the surface of the protected support.

The object of the present invention is to provide the man skilled in the art with a biocidal compound which can be incorporated in particular in paints, which is compatible with a large number of basic binders and which is definitely of better anti-contamination action than the biocidal compounds known at the present time.

The object of the invention is therefore an organometallic telomer which can be used in particular as biocidal agent, characterized by the fact that it is represented by the general formula

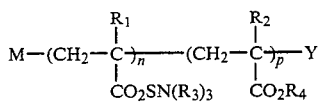

in which n and p represent numbers between 1 and 100 such that the ratio $n/n+p$ is less than or equal to 0.75;

$R_1$ and $R_2$, which may be identical or different, represent a hydrogen atom or a methyl group;

$R_3$ represents a linear or branched alkyl group of 1 to 12 carbon atoms, or a substituted or unsubstituted phenyl group;

$R_4$ represents a hydrogen atom or has one of the meanings indicated for $R_3$;

M and Y coming from a transfer agent in which Y represents hydrogen, chlorine or bromine and M an electroattractive organic group.

M may advantageously be selected from among the following electroattractive organic groups:

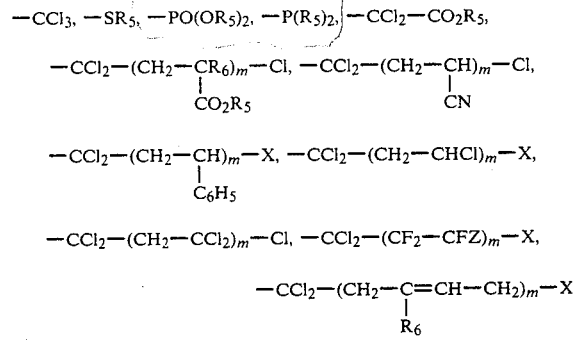

in which m represents a whole number between 1 and 100, $R_5$ a hydrogen atom or an alkyl group containing 1 to 12 carbon atoms, $R_6$ a hydrogen atom or a methyl group, Z either chlorine or fluorine and X either chlorine or hydrogen.

More particularly, m may be between 1 and 10 and $R_5$ is a methyl, ethyl, propyl or butyl group.

A preferred family of telomers is that in which:
Y represents chlorine
M is selected from among the groups $-CCl_3$, $-CCl_2-CF_3$, $-CCl_2-COOCH_3$, $-CCl_2-CH_2-CHCl-COOCH_3$, $-CCl_2-(CF_2-CFZ)_m-Cl$ in which $m=1$, 2 or 3 and Z represents either chlorine or fluorine;
$R_3$ represents an ethyl, propyl or butyl group;
$R_4$ represents hydrogen or a methyl group.

Another preferred family of telomers is that in which:
Y represents hydrogen or bromine;
M represents one of the groups $-CCl_3$ and $-PO(OC_2H_5)_2$,
$R_3$ represents an ethyl, propyl or butyl group;
$R_4$ represents hydrogen or a methyl group.

Another object of the invention are methods of preparing the telomers defined above.

In accordance with one method, a transfer agent (II), an organostannic monomer (III) and an acrylic comonomer (IV) are reacted with each other.

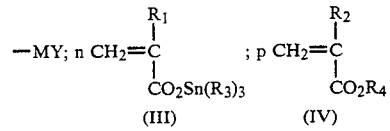

M, Y, $R_2$, $R_3$ and $R_4$ having the meanings indicated above, in the presence of a catalyst formed of a metal powder or a metal salt in which the metal is capable of oxidizing, and a polar solvent for about 24 ;1 to 48 hours, at a temperature close to the boiling point of the mixture.

The polar solvent is advantageously selected from among nitriles such as acetonitrile, propionitrile and butyronitrile, the catalyst being selected from among the group formed of iron, copper, magnesium, cuprous chloride, ferrous chloride, potassium ferrocyanide, cupric chloride, potassium ferricyanide or else ferric chloride in the presence of a reducing agent such as benzoin.

The ratio of the concentrations of the catalyst to the monomers is preferably betwen $3 \cdot 10^{-3}$ and $3 \cdot 10^{-2}$.

In accordance with another method, a transfer agent (II), an organostannic monomer (III) and an acrylic comonomer (IV)

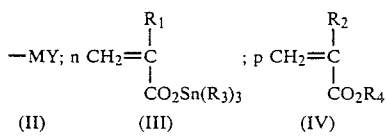

are reacted together

M, Y, $R_1$, $R_2$, $R_3$, $R_4$ having any of the meanings indicated above, in the presence of a catalyst formed of a radical initiator of the benzoyl peroxide or azobis-isobutyronitrile type and a radical telomerization solvent of the benzene, toluene and xylene type for about 5 to 10 hours at a temperature close to the boiling point of the mixture.

The ratio of the concentrations of the transfer agent (II) and the organostannic monomers is advantageously between 2 and 10.

In accordance with still another method, a transfer agent MY (II) is reacted in a first step with an acrylic monomer (V) in order to obtain a telomer (VI) in accordance with the reaction

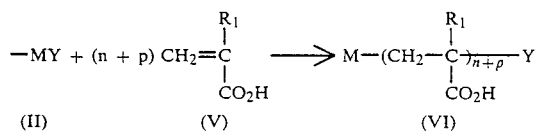

M, Y, n, p, $R_1$ having any of the meanings indicated above. The reaction is carried out in the presence of a catalyst formed of a metal powder or a metal salt in which the metal is capable of oxidizing, and a polar solvent, the mixture obtained being maintained under reflux for 10 to 48 hours; in a second step, the telomer obtained is treated with an organostannic derivative (VII) in accordance with the reaction

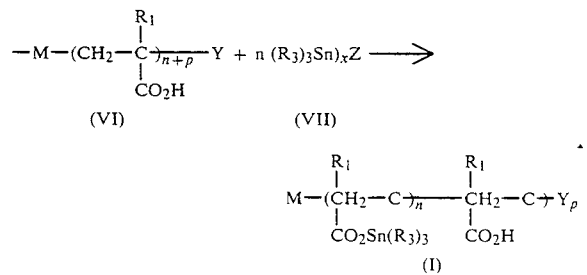

$R_3$ having the meaning indicated above and in which $x=2$, $Z=O$ or else $x=1$, $Z=Cl$, in the presence of a polar solvent such as, for instance, tetrahydrofuran, the mixture obtained being held under reflux for about 10 to 48 hours.

Still another object of the invention are biocidal compositions comprising an organometallic telomer such as defined or obtained previously, to control parasitic organisms.

A paint intended to control the growth of organisms advantageously comprises a base of conventional type and about 15 to 30% by weight of the organometallic telomer in accordance with the invention.

A leading advantage of the invention resides in the fact that the telomer of the invention is used as additive to conventional paint bases, which use is entirely novel in the art of paints. As a result thereof, the coat of paint is not degraded by hydrolysis.

Another advantage resides in the fact that the active principle is bound chemically to an additive which is compatible with most conventional binders. As a result the doses required are less for the same action, which further decreases the pollution of the environment.

Other advantages relate specifically to the use of the telomers of the invention. First of all, there will be noted the adherence to metals, which is very definitely improved as a result of the presence of residual acid groups. Then there will be noted the possibility of modulating the properties as a function of the effect desired. Thus, if one is interested in qualities of slipperiness one would prefer telomers comprising fluorinated telogens which are directed towards the surface of the support, which therefore decreases the surface energy. On the other hand, if one desires to promote compatibility of the telomer with a particular base resin or adhesiveness of the coat of paint to the previous coats, it is sufficient to provide a telogenic agent comprising the same monomers as the binder of the base paint or of the previous coats.

As is already evident from the foregoing, the molecular weight of the telomers of the invention can be adjusted within a very wide range of values and this in a substantially non-polydispersed manner. The molecular weight is therefrom completely controllable and can be determined in advance.

Finally, the nature of the transfer agent permits access to bisequential telomers or cotelomers containing specific atoms or sequences which can impart particular properties to them.

In the present description there is understood by telomer (or cotelomer) a polymer the ends of which are fully known and come from a transfer agent, known as a telogen which gives two complementary radicals, the degree of polymerization of this polymer being less than 100.

Various methods make it possible to prepare the telomers of the invention. By way of illustration, three particular methods of synthesis which the man skilled in the art can, of course, adapt have been cited. It will be noted, however, that in certain cases the nature of the transfer agent used imposes a particular manner of procedure. In accordance with a first manner, the telomerization can be effected by redox catalysis, which requires the use of a polar solvent in order to solubilize the catalyst. Nitriles will preferably be employed and among them the aliphatic nitriles such as acetonitrile propionitrile and butyronitrile. In this case the solvent is miscible with the reagents and does not enter into competition with the telogenic agent upon the transfer reactions. The catalyst is preferably either a metal powder, in particular iron, copper or magnesium, or a metal salt in which the metal is capable of passing to a higher degree of oxidation, in particular cuprous chloride, ferrous chloride and potassium ferricyanide. Another solution consists in using a metal salt which is reducible by a reducing agent such as benzoin; this metal salt may be ferric chloride. In order to carry out this first manner of procedure, cotelomerization of an organostannic monomer is effected with various acrylic or other comonomers. The organostannic comonomer is, as indicated, a triorganostannic acrylate or methacrylate, for instance triethyl tin, tripro-pyl tin tri-n-butyl tin or triphenyl tin acrylate or methacrylate; the tin, of course, may bear different radicals. The comonomer of the acrylic type is preferably a methyl, ethyl, or propyl acrylate or methacrylate, or acrylic or methacrylic acid. The preferred transfer agent in this case is $CCl_4$, $CF_3CCl_3$, $CCl_3$=$CO_2CH_3$, $CCl_3$—$CH_2$—$CHCl$—$CO_2CH_3$, or $CCl_3$—$(CF_2$—$CFZ)_m$—$Cl$ in which $m=1$, 2 or 3 and Z represent either chlorine or fluorine.

A theoretical study of redox catalysis has shown that the degree of polymerization of the telomer may be adjusted as desired since it depends solely on the ratio of the respective initial concentrations of catalyst and monomers. It is preferred that this ratio be between $3 \cdot 10^{-3}$ and $3 \cdot 10^{-2}$. The telomers obtained then have a degree of polymerization of between 10 and 100. However, it should be noted that the nature of the catalyst influences the molecular weight of the telomer obtained. Thus it has been found that catalysis with cuprous or cupric salts leads in general to telomers of low molecular weight. On the other hand, catalysis with potassium ferrocyanide or ferricyanide makes it possible to obtain telomers of a number average degree of polymerization $\overline{DP}_n$ of the order of 50 to 100. With ferrous or ferric salts, the $\overline{DP}_n$ is on the order of 10 to 50.

In accordance with a second embodiment, the telomerization can be effected by radical initiation. The initiators used are those of the conventional radical catalysis, among which benzoyl peroxide or azobisisobutyronitrile is preferred. The same is true of the solvents, and use has been made in particular of benzene, toluene and acetonitrile. The organostannic monomer and the acrylic comonomer are those indicated previously.

When a radical telomerization is carried out, it is noted that the molecular weight of the telomer obtained depends on the ratio of the concentration of the telogen to the monomer. The length of the chain may therefore be adjusted as desired. It is preferred that this ratio be between 2 and 10, which makes it possible to obtain a $\overline{DP}_n$ on the order of 10 to 50. It has been found that the molecular weights obtained with radical catalysis are generally higher than with redox catalysis under comparable conditions. However, the characteristics are substantially close. Thus when the ratio n/p is less than 0.66 (60% comonomer in the telomer) the telomer is in the form of a powder. Below 60% comonomer in the telomer, the latter is in the form of more or less viscous waxes. When $R_4$ is an alkyl, the telomers are always in the form of waxes. Of course, an increase in the degree of polymerization increases the viscosity of these waxes, which may become extremely viscous.

In accordance with a third embodiment, the telomer of the invention can be obtained by grafting organostannic compounds on a support telomer having reactive functions. By way of example, a telomer having reactive functions of the carboxylic acid type can be reacted with bis-triorgano-tin oxide. For this purpose one proceeds in the following or an equivalent manner. The support telomer is first of all prepared in accordance with the following scheme:

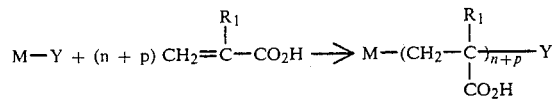

The reaction takes place in a first step by redox catalysis and the catalysts and solvents mentioned in the first embodiment are used and the degree of polymerization is adjusted in identical fashion.

The number average degree of polymerization $\overline{DP}_n$ of these telomers varies between 10 and 100 when a mixture of ferric trichloride and benzoin is used as catalyst system. This $\overline{DP}_n$ can be extremely variable when the copper salts are used; thus, for example, it is equal to 1 and 3 respectively in the case of methacrylic and acrylic acids when the ratio of the concentrations of catalyst to monomer is close to $10^{-2}$ and is equal to 30 and 50 respectively when this ratio is close to $10^{-3}$.

In a second step, the bis-triorgano-tin oxide is attached by esterification in accordance with the reaction:

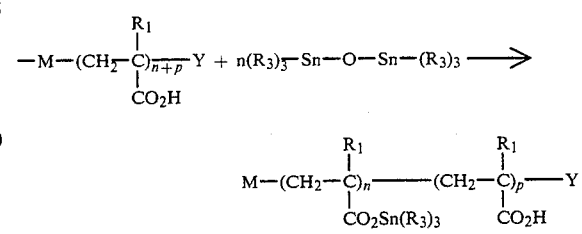

M, Y, $R_1$, $R_3$, n and p having the meanings indicated above and the reaction taking place in a polar solvent, such as tetrahydrofuran for a period of 10 to 48 hours at a temperature close to 70° C.

At the end of the reaction, the substituted telomer is isolated by precipitation from a non-solvent such as pentane.

These telomers are in the form of powders or viscous liquids depending on the number of esterified functions; the rate of esterification in no case exceeds 70%.

The following examples illustrate particular embodiments.

EXAMPLE 1

The cotelomerization is effected by redox catalysis of tributyl tin acrylate and methyl acrylate.

In this example, the telogenic agent used is carbon tetrachloride.

15.82 g (0.044 mole) of tributyl tin acrylate, 3.97 g (0.046 mole) of methylacrylate, 0.062 g ($4 \cdot 10^{-4}$ mole) of ferric trichloride, 0.083 g ($4 \cdot 10^{-4}$ mole) of benzoine, 4.41 g ($2.86 \cdot 10^{-2}$ mole) of carbon tetrachloride and 150 ml of acetonitrile are added one after the other into a 250 ml flask provided with condenser.

The reaction mixture is maintained at a boil for 24 hours. After cooling and evaporation of the solvent, 17.8 g of cotelomer are collected (number average molecular weight $\overline{M}_n = 16,000$). The product is in the form of a brown wax and the yield of the reaction is 90%. The substituents are therefore as follows:

$R_1$=H; $R_2$=H; $R_3$=$C_4H_9$; $R_4$=$CH_3$; M=$CCl_3$; Y=Cl.

EXAMPLE 2

The cotelomerization is effected by redox catalysis of tributyl tin acrylate and acrylic acid. The same procedure is used as in Example 1 merely replacing the methylacrylate by acrylic acid. The cotelomer obtained has a number average molecular weight $\overline{M}_n$ of 13,000 and is also in the form of a brown wax. The yield is also 90%. The substituents are therefore the following:

$R_1=H$; $R_2H$; $R_3=C_4H_9$; $R_4=H$; $M=CCl_3$; $Y=Cl$.

EXAMPLE 3

The cotelomerization is effected by redox catalysis of tributyl tin acrylate and methacrylic acid. The same procedure is used as in Example 1, merely replacing the methacrylate by methacrylic acid.

The cotelomer obtained has a number average molecular weight $\overline{M}_n$ of 10,000 and is also in the form of a brown wax. The yield is 90%. The substituents are therefore the following:

$R_1=H$; $R_2=CH_3$; $R_3=C_4H_9$; $R_4=H$; $M=CCl_3$; $Y=Cl$.

EXAMPLE 4

The three previous cotelomerizations are carried out of redox catalysis, using the following telogenic agents:

$Cl(CFCl-CF_2)_m-CCl_3$, $CF_3-CCl_3$,

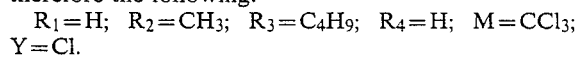

$CCl_3-CH_2-CHCl-COOCH_3$; $m=1, 2$ or $3$.

Cotelomers are obtained with average molecular weights $\overline{M}_n$ on the order of 10,000 to 20,000. They are all in the form of wax. The yield varies from 75% to 90% depending on the telogenic agent used.

EXAMPLE 5

The cotelomerization is effected by redox catalysis of tributyl tin acrylate and methacrylic acid. The same procedure is used as indicated in Example 1, varying the percentages of monomers.

7.22 g (0.02 mole) of tributyl tin acrylate, 8.6 g (0.1 mole) of methacrylic acid, 0.087 g ($5 \cdot 10^{-4}$ mole) of ferric trichloride, 0.113 g ($5 \cdot 10^{-4}$ mole) of benzoine, 5.96 g ($3.87 \cdot 10^{-2}$ mole) of carbon tetrachloride and 150 ml of acetonitrile are introduced one after the other into a 250 ml flask provided with a condenser.

The reaction mixture is maintained at a boil for 24 hours. After cooling and precipitation of the product in pentane there are collected 14.4 g of cotelomer (number average molecular weight $\overline{M}_n=14,000$). The product is in the form of a brown wax and the yield of the reaction is close to 90%. The substituents are therefore the following:

$R_1=H$; $R_2=CH_3$; $R_3=C_4H_9$; $R_4=H$; $M=CCl_3$; $Y=Cl$.

EXAMPLE 6

The cotelomerization is effected by redox catalysis of triphenyl tin acrylate with acrylic acid. The same procedure is used as in Example 2, merely replacing the tributyl tin acrylate by triphenyl tin acrylate. The cotelomer obtained has a number average molecular weight $\overline{M}_n$ close to 20,000 and the yield is close to 80%. The substituents are therefore the following:

$R_1=H$; $R_2=H$; $R_3=C_6H_5$; $R_4=H$; $M=CCl_3$; $Y=Cl$.

EXAMPLE 7

The cotelomerization is effected by radical initiation of tributyl tin acrylate with acrylic acid.

16 g ($4.43 \cdot 10^{-2}$ mole) of tributyl tin acrylate, 4.32 g ($6 \cdot 10^{-2}$ mole) of acrylic acid, 2.76 g ($2 \cdot 10^{-2}$ mole) of diethyl phosphonate, 2.42 g ($10^{-2}$ mole) of benzoyl peroxide and 150 ml of benzene are introduced into a 250 ml flask.

The mixture is maintained at a boil for six hours. After cooling and evaporation of the solvent, the product is washed several times with ether. 17 g of cotelomer are collected which is in the form of a white powder. The yield is about 85%. The number average molecular weight $\overline{M}_n$ is close to 90,000. The substituents are therefore the following: $R_1=H$; $R_2=H$; $R_3=C_4H_9$; $R_4=H$; $M=(C_2H_5O)_2(O)P-$; $Y=H$.

EXAMPLE 8

The cotelomerization is effected by radical initiation of tributyl tin acrylate with methyl acrylate. The same procedure is used as set forth in Example 7, merely replacing the acrylic acid by methylacrylate. The cotelomer obtained has a number average molecular weight $\overline{M}_n$ of 100,000 and is present also in the form of a white powder. The yield is 85%. The substituents therefore are:

$R_1=H$; $R_2=H$; $R_3=C_4H_9$; $R_4=CH_3$; $M(C_2H_5O)_2(O)P-$; $H$.

EXAMPLE 9

The two previous cotelomerizations are effected by radical initiation, merely replacing the telogenic agent by $CCl_3-Br$. Two cotelomers are obtained of a number average molecular weight substantially equal to 1000. The yield is identical. The substituents are therefore in both cases:

$R_1=H$; $R_2=H$; $R_3=C_4H_9$; $R_4=H$; $M=CCl_3$; Br and
$R_1=H$; $R_2=H$; $R_3=C_4H_9$; $R_4=CH_3$; $M=CCl_3$; $Y=Br$.

EXAMPLE 10

The cotelomerization is effected by radical initiation of tributyl tin acrylate with acrylic acid. The same procedure is used in Example 7, varying the molar ratio of telogen to monomer.

The same quantities of tributyl tin acrylate, acrylic acid, benzoyl peroxide and benzene as in Example 7 are introduced into a 250 ml flask. 14.35 g (0.104 mole) of diethylphosphonate are added to the mixture.

The mixture is maintained at a boil for six hours. After cooling, evaporation of the solvent and washing with ether, 18 g of cotelomer are collected (yield: 90%) of a number average molecular weight $\overline{M}_n$ close to 6000. The substituents are identical to those of Example 7.

EXAMPLE 11

1. Synthesis of the Support Telomers 6.59 moles (567 g) of methacrylic acid, 0.0516 mole (8.38 g) of ferric chloride, 0.0516 mole (10.93 g) of benzoine, 0.826 mole (127.20 g) of carbon tetrachloride and 1200 ml of acetonitrile are introduced into a 3-liter flask. It is kept under reflux with agitation for one hour. After cooling, the telomer which precipitates is filtered. The filtrate is returned to the reaction. The telomer which is formed precipitates again. At the end of seven filtrations, 500 g of support telomers are obtained. These telomers are in the form of white powders ($\overline{M}_n=3600$) (yield: 85%).

2. Reactions of Tributyl Tin Oxide

The fraction of the telomers of methacrylic acid which is soluble in tetrahydrofuran ($\overline{DP}_n=27$) is used for this reaction.

200 g ($8 \cdot 10^{-2}$ mole) of support telomer, 260 g ($4.36 \cdot 10^{-1}$ mole) of tributyl tin oxide and 2 liters of tetrahydrofuran are introduced into a 3-liter flask. It is kept at reflux for 48 hours. After cooling and partial evaporation of the solvent, the product is precipitated from petroleum ether. 380 g of 40% grafted cotelomer are collected (yield: 83%). These cotelomers are in the form of white powders. The substituents are therefore the following:

$R_1=R_2=CH_3$; $R_3=C_4H_9$; $R_4=H$; $M=CCl_3$; $Y=Cl$ and $n=10.8$ and $p=16.2$.

EXAMPLE 12

A cotelomer is produced in the manner described in Example 11 using, however, 455 g of tributyl tin oxide. The grafting rate is then 70% and 525 g of waxy cotelomer are obtained after evaporation of the solvent (yield: 80%).

EXAMPLE 13

A cotelomer is produced in the manner set forth in Example 11, replacing the telomers of methacrylic acid, however, by telomers of acrylic acid ($\overline{DP}_n=50$). A cotelomer is obtained which is also in the form of a white powder with an average molecular weight $\overline{M}_n$ of 8000. The yield is substantially close to 75%. The substituents are:

$R_1=R_2=H$; $R_3=C_4H_9$; $R_4=H$; $M=CCl_3$; $Y=Cl$, $n=15.5$; $p=34.5$.

EXAMPLE 14

Example 13 is repeated, merely changing the proportion of tributyl tin oxide. A series of cotelomers which differ only in the percentage of grafting can be prepared in this way. Cotelomers were prepared in which $n=10.8$ and $p=39.2$, and then $n=12.8$ and $p=37.2$ and then $n=19.5$ and $p=30.5$ and then $n=30.9$ and $p=19.1$.

The first three of these cotelomers are in the form of a white powder while the latter is a viscous wax.

EXAMPLE 15

A cotelomer is prepared in the manner taught in Example 11 using, however, fluorinated telogens of the type $Cl-(CFZ-CF_2)_m-CCl_3$ in which $m=1$, 2 or 3 and Z is either chlorine or fluorine.

6.59 moles (567 g) of methacrylic acid, 0.0516 mole (8.38 g) of ferric chloride, 0.0516 mole (10.93 g) of benzoine, 0.83 mole (417 g) of telomer $Cl-(CFCl-CF_2)_3-CCl_3$ and 1200 ml of acetonitrile are introduced into a 3-liter flask. The mixture is refluxed with agitation for 24 hours. After cooling and partial evaporation of the solid, the cotelomer is precipitated from hexane. Upon filtration there are obtained 690 g of cotelomer of a number average molecular weight of $\overline{M}_n=2300$ (yield 70%).

After solubilization of this cotelomer in tetrahydrofuran 715 g (1.2 mole) of tributyl tin oxide are added. It is kept at reflux for 48 hours. After cooling and evaporation of the solvent, 1125 g of 40% grafted cotelomer are obtained (yield: 80%).

The substituents are therefore:

$R_1=CH_3$; $R_2=CH_3$; $R_3=C_4H_9$; $R_4=H$; $M=Cl-(CFCl-CF_2)_3-CCl_2-$; $Y=Cl$; $n=8$, $p=12$.

EXAMPLE 16

A cotelomer substituted by tributyl tin chloride is prepared from support telomers having reactive functions.

1. Synthesis of Support Telomers

The same procedure is used as in Example 11.1.

2. The reaction of tributyl tin chloride on the support telomer is carried out as in Example 11.2. In this way cotelomers having graft percentages varying between 10 and 70% are obtained with yields on the order of 80%.

The telomers obtained in accordance with the invention have been tested both in the laboratory and in a natural environment. In the laboratory the rate of hydrolysis or lixiviation of the active principle incorporated in a biocidal paint was studied and the element liberated was determined by pulse polarography. It was found in general that paints containing cotelomers in accordance with the invention gave off a practically constant amount of tin during the course of the 800 test hours. On the other hand, a commercial biocidal paint subjected to the same tests gives off during the initial hours a large amount of tin, which amount decreases rapidly in the course of time.

| TIME IN HOURS | | 24 | 137 | 262 | 433 | 642 | 882 |
|---|---|---|---|---|---|---|---|
| COMMERCIAL PAINT | $H_i^*$ | 272.5 | 702.5 | 1135 | 1485 | 1760 | 2065 |
| PAINT OF THE INVENTION | $H_i^*$ | 50.2 | 139.2 | 202.7 | 295.7 | 407.2 | 564.7 |

$H_i^*$: Height of the polarograph wave. $H_i$ is directly proportional to the mass of active principle released. As to the type released it was established that it consisted solely of the cation $R_3Sn^+$ when the telomer of the invention is used; on the other hand the commercial paint studied by way of comparison gives off insoluble tributyl tin oxide into the atmosphere and is therefore less active.

In a natural environment a plate comprising three zones was immersed to a depth of about 70 cm at a place where the submarine fauna and flora were in full growth: a first unprotected zone, a second zone covered by a commercial biocidal paint and a third zone covered by a paint containing a conventional base and a cotelomer in accordance with the invention.

At the end of six months the first control zone was entirely covered with marine organisms, the second zone was partially covered, while the third zone was intact. One year later, the first control zone was covered to a thickness of about 7 cm with marine organisms and the second zone to a thickness of about 3 cm; the third zone was intact. This demonstrates the superiority of the biocidal agent formed by the telomer in accordance with the invention.

We claim:

1. A biocidal organometallic telomer of the formula (I):

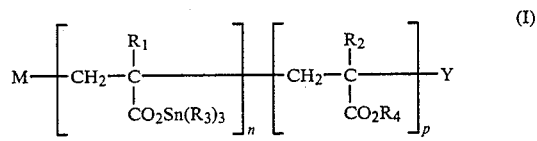

wherein, n and p represent numbers between 1 and 100 wherein the ratio is n/(n+p) less than or equal to 0.75;

$R_1$ and $R_2$ are independently selected from the group consisting of hydrogen and methyl;

$R_3$ is selected from the group consisting of substituted and unsubstituted linear and branched chain alkyl having from 1 to 12 carbon atoms and substituted and unsubstituted phenyl;

$R_4$ is selected from the group consisting of substituted and unsubstituted linear and branched chain alkyl having from 1 to 12 carbon atoms, substituted and unsubstituted phenyl and hydrogen;

M and Y are derived from a transfer agent, wherein:
  Y is selected from the group consisting of hydrogen, chlorine and bromine; and
  M is an electroattractive organic group selected from the group consisting of $CCl_3$, $SR_5$, $PO(OR_5)_2$, $P(R_5)_2$, $CCl_2CO_2R_5$,

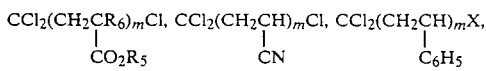

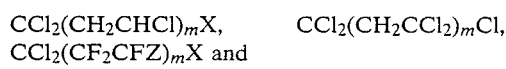

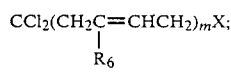

wherein, m represents a whole number between 1 and 100, $R_5$ is selected from the group consisting of hydrogen and alkyl having from 1 to 12 carbon atoms, $R_6$ is selected from the group consisting of hydrogen and methyl, Z is selected from the group consisting of chlorine and fluorine, and X is selected from the group consisting of chlorine and hydrogen.

2. A biocidal organometallic telomer of the formula (I):

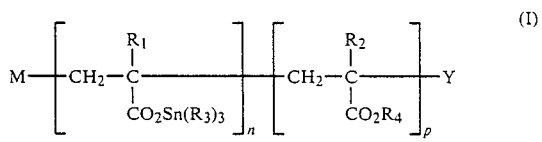

wherein:
  n and p represent numbers between 1 and 100 wherein the ratio n/(n+p) is less than or equal to 0.75;
  $R_1$ and $R_2$ are independently selected from the group consisting of hydrogen and methyl;
  $R_3$ is selected from the group consisting of ethyl, propyl and butyl;
  $R_4$ is selected from the group consisting of hydrogen and methyl;
  M and Y are derived from a transfer agent, wherein:
    Y represents chlorine; and
    M is an electroattractive organic group selected from the group consisting of —$CCl_3$, —$CCl_2$—$CF_3$, —$CCl_2$—$COOCH_3$, —$CCl_2$—$CH_2$—$CHCl$—$COOCF_3$ and —$CCl_2$—$(CF_2$—$CFZ)_m$—$Cl$;
    wherein,
    m represents a whole number from 1 to 3; and
    Z is selected from the group consisting of chlorine and fluorine.

3. The organometallic telomer of claim 1, wherein m represents a whole number between 1 and 10 and $R_5$ is selected from the group consisting of methyl, ethyl, propyl and butyl.

4. The organometallic telomer of claim 3, wherein:
  Y is selected from the group consisting of hydrogen and bromine;
  M is selected from the group consisting of —$CCl_3$ and $PO(OC_2H_5)_2$;
  $R_3$ is selected from the group consisting of ethyl, propyl and butyl; and,
  $R_4$ is selected from the group consisting of hydrogen and methyl.

* * * * *